US008529554B2

(12) United States Patent
Murakami et al.

(10) Patent No.: US 8,529,554 B2
(45) Date of Patent: Sep. 10, 2013

(54) TREATMENT INSTRUMENT OPERATION UNIT AND MEDICAL SYSTEM WITH TREATMENT INSTRUMENT OPERATION UNIT

(75) Inventors: Kazushi Murakami, Hino (JP); Yoshio Onuki, Hachioji (JP); Takaaki Komiya, Akiruno (JP); Hiroaki Ichikawa, Yokohama (JP); Tsutomu Okada, Tachikawa (JP); Kazuki Honda, Hachioji (JP); Yasuhito Kura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1770 days.

(21) Appl. No.: 11/850,366

(22) Filed: Sep. 5, 2007

(65) Prior Publication Data
US 2009/0062603 A1 Mar. 5, 2009

(51) Int. Cl.
A61B 17/00 (2006.01)
A61B 17/295 (2006.01)
A61B 1/018 (2006.01)
A61B 17/29 (2006.01)

(52) U.S. Cl.
USPC .............................. 606/1; 600/104; 600/106

(58) Field of Classification Search
USPC ..................................... 606/1; 600/104, 106
See application file for complete search history.

(56) References Cited

U.S. PATENT DOCUMENTS

| 5,431,645 | A | * | 7/1995 | Smith et al. ..................... 606/1 |
| 2002/0107538 | A1 | * | 8/2002 | Shibata et al. ................ 606/169 |
| 2003/0050654 | A1 | * | 3/2003 | Whitman et al. ............. 606/167 |
| 2004/0092912 | A1 | | 5/2004 | Jinno et al. |
| 2005/0192475 | A1 | * | 9/2005 | Okada ........................... 600/106 |
| 2006/0106281 | A1 | * | 5/2006 | Boulais et al. ................ 600/104 |

FOREIGN PATENT DOCUMENTS

| EP | 0 943 293 A1 | 9/1999 |
| JP | 2004-208922 | 7/2004 |
| JP | 2007-125180 | 5/2007 |

OTHER PUBLICATIONS

Extended European Search Report dated Feb. 4, 2010.

* cited by examiner

Primary Examiner — Henry M Johnson, III
Assistant Examiner — William Cheng
(74) Attorney, Agent, or Firm — Scully, Scott, Murphy & Presser, P.C.

(57) ABSTRACT

A treatment instrument operation unit is provided with a drive unit, an operation portion installation section and a command signal output section. The drive unit drives an operation portion for operating each treatment section of the respective treatment instruments. The operation portion is attached to the operation portion installation section provided to the drive unit. The command signal output section outputs an installation start signal to a controller for notifying that the installation of the treatment instrument has begun upon installation of the operation portion in the operation portion installation section. After outputting the installation start signal from the command signal output section to the controller, the drive unit drives the operation portion installation section to the position where the operation portion is allowed to be installed based on the control signal outputted form the controller.

5 Claims, 5 Drawing Sheets

TREATMENT INSTRUMENT OPERATION UNIT AND MEDICAL SYSTEM WITH TREATMENT INSTRUMENT OPERATION UNIT

BACKGROUND OF THE INVENTION

1. Field of the Invention

The present invention relates to a medical device equipped with a treatment instrument for treating the body tissue, and particularly to an endoscope inserted into a body cavity, a treatment instrument operation unit which serves to open and close treatment sections of various kinds of the treatment instrument used together with the endoscope, and a medical system equipped with the treatment instrument operation unit.

2. Description of the Related Art

It is well known that the endoscope has been widely used in the industrial field or the medical field. As the medical equipment used in the medical field, the endoscope has an insertion portion inserted into the body cavity of the subject body so as to perform various kinds of treatments by inserting the treatment instrument into the body cavity via the treatment instrument channel formed in the insertion portion of the endoscope while performing the observation.

In the case where the body tissue is treated with the treatment instrument, the operator introduces the treatment instrument into the body cavity via the treatment instrument channel of the endoscope so as to take the body tissue or perform the treatment.

The operator inserts the treatment instrument into the body cavity while grasping an operation portion of the endoscope with one hand. The operator holds the sheath as the insertion portion of the treatment instrument with the other hand such that the sheath is manually inserted into the treatment instrument channel. The proximal end side of the sheath is held by the staff such as the nursing staff so as to prevent the sheath with the length of 2 m, for example, from being partially brought into contact with the unclean area such as the floor upon insertion.

The operator will take the body tissue with the treatment instrument while grasping the endoscope operation portion with one hand. It is impossible for the operator to operate the operation portion of the treatment instrument while holding the insertion portion of the endoscope with the other hand. For this reason, the staff is expected to hold the insertion portion of the endoscope or operate the operation portion of the treatment instrument. That is, assistance of the staff is inevitable for inserting the sheath of the treatment instrument into the treatment instrument channel of the endoscope, and operating the treatment instrument inserted into the treatment instrument channel.

Publication of U.S. Pat. No. 5,431,645 discloses the device for performing the automatic remote control of the endoscopic operation system such as the endoscope biopsy forceps device. The automatic remote controller allows the surgeon, for example, to operate the biopsy forceps by handling the operation means through the foot pedal or the voice command, for example.

Recently, the remote control with respect to various kinds of the treatment instruments, for example, the high frequency knife, the rotary clip and the like using the automatic remote controller has been increasingly demanded. The distance between installation positions of the thumb ring and the slider which form the operation portion of the treatment instrument, and the maximum displacement distance may vary depending on the type of the treatment instrument. The operator is required to coincide the installation position of the operation portion installation section attached to the remote unit with the operation portion of the treatment instrument every time when the treatment instrument is installed in the automatic remote control unit.

SUMMARY OF THE INVENTION

A treatment instrument operation unit according to the present invention includes a drive unit, an operation portion installation section and a command signal output section. The drive unit drives an operation portion for operating each treatment section of the respective treatment instruments. The operation portion is attached to the operation portion installation section. The operation portion installation section is provided to the drive unit. The command signal output section outputs an installation start signal to the controller upon installation of the operation portion to the operation portion installation section, notifying that installation of the treatment instrument has begun. Subsequent to the output of the installation start signal to the controller from the command signal output section, the drive unit drives the operation portion installation section to the position at which the operation portion is allowed to be installed based on the control signal outputted from the controller.

A medical system according to the present invention includes plural kinds of treatment instruments, a treatment instrument operation unit and a controller. Each of the plural kinds of treatment instruments has a different treatment section. The treatment instrument operation unit includes a drive unit, an operation portion installation section and a command signal output section. The drive unit drives the operation portion for operating the treatment section of the treatment instrument. The operation portion of the treatment instrument is installed in the operation portion installation section. The command signal output section outputs an installation start signal upon start of installation of the treatment instrument in the operation portion installation section. The controller is connected to the treatment instrument operation unit. The controller is equipped with the control unit including a treatment instrument information memory unit and a signal output section. The treatment instrument information memory unit stores information of plural types of treatment instruments including the installation distance and the maximum displacement distance as the position information of the operation portion, which has been preliminarily set with respect to the type and model of the treatment instrument. The signal output section obtains the treatment instrument information from the respective kinds of treatment instrument information data stored in the treatment instrument information memory unit for outputting the control signal to the drive unit.

The above and other objects, features and advantages of the invention will become more clearly understood from the following description referring to the accompanying drawings.

DETAILED DESCRIPTION OF PREFERRED EMBODIMENTS

The preferred embodiments of the present invention will be described referring to the drawings.

The embodiment of the present invention will be described referring to FIGS. 1 to 6.

Figure 1:
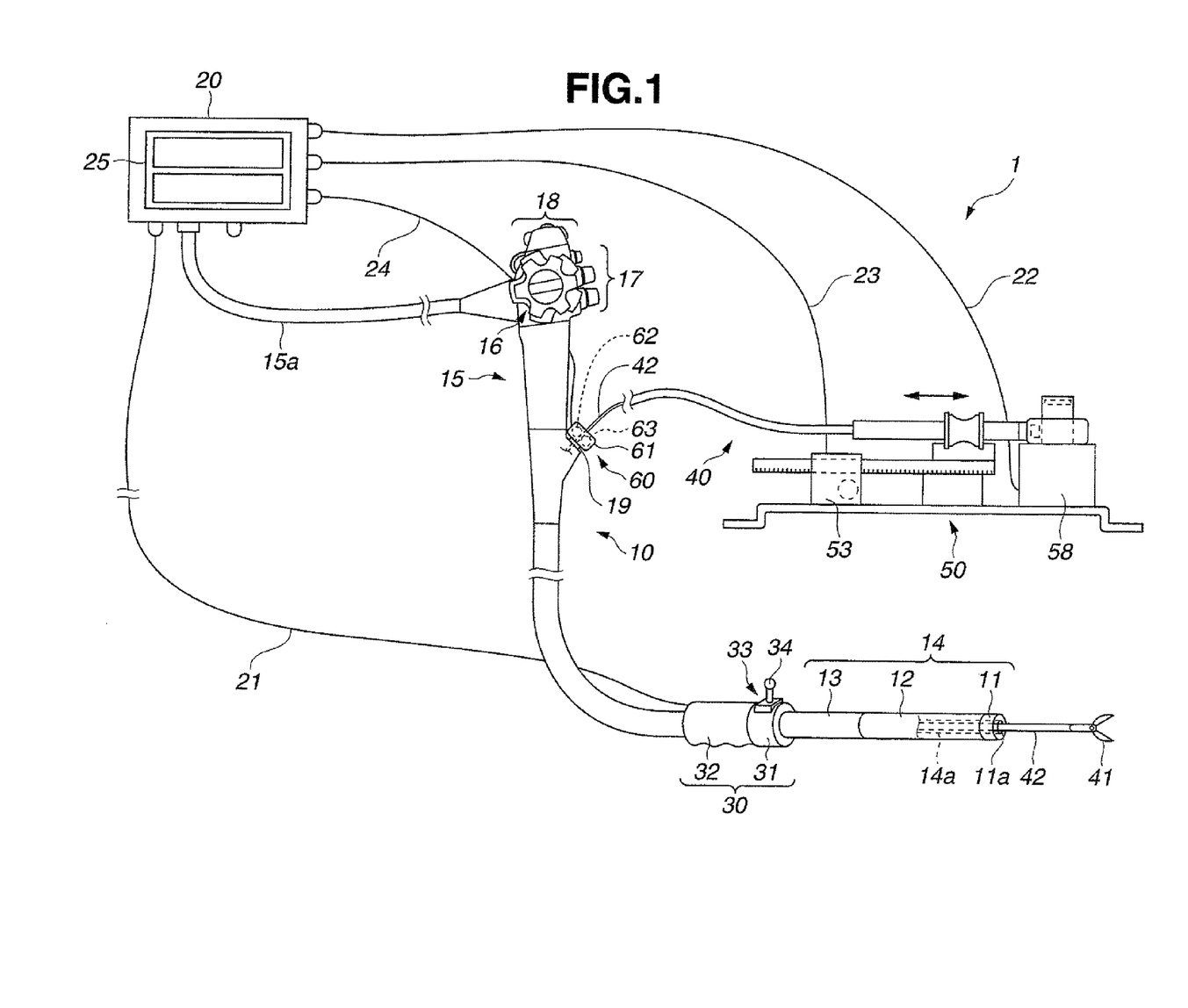
FIG. 1 is a view of a medical system equipped with a treatment instrument operation unit.

Referring to FIG. 1, a medical system 1 according to the embodiment is mainly formed of an endoscope 10, a controller 20 equipped with a light source device and a video processor, a control 30 serving as an operation command unit, a treatment instrument 40 equipped with a treatment section 41 for performing a predetermined treatment to the body tissue, a treatment instrument operation unit 50 serving as a treatment section operation unit for power-driving the treatment section 41, and a treatment instrument insertion portion power drive unit (hereinafter simply referred to as a power drive unit) 60 serving as a treatment instrument drive unit for driving a treatment instrument insertion portion, that is, a sheath 42 of the treatment instrument 40.

The endoscope 10 includes an endoscope insertion portion (hereinafter simply referred to as an insertion portion) 14 formed by connecting a distal end portion 11, a bending portion 12 and a flexible tube 13 in the order from the distal end side. The distal end portion 11 is formed of a rigid member and has a distal end opening 11a formed in its distal end. The bending portion 12 is bendable in the vertical and lateral directions. The flexible tube 13 exhibits flexibility. An operation portion 15 is connected to the proximal end of the insertion portion 14.

The operation portion 15 is also used as a grasping portion to be grasped by the operator. A universal cord 15a extending from the operation portion 15 has a not shown connector provided to the proximal end so as to be detachable with respect to the controller 20. The operation portion 15 is provided with two bending knobs 16 for bending the bending portion 12 in the vertical and the lateral directions, respectively, fluid control buttons 17 including an air/water feed button for feeding air/water, a suction button for suction and the like, and various switches 18 for controlling with respect to the endoscopic images provided from a not shown image pickup device at the distal end portion 11. The operation portion 15 is provided with a treatment instrument insertion port 19 at the insertion portion side communicated with the proximal end of a treatment instrument channel 14a in the insertion portion 14. The distal end of the treatment instrument channel 14a is communicated with the distal end opening 11a.

The control 30 is structured to be freely arranged with respect to the insertion portion 14 of the endoscope 10. The control 30 is formed of a rigid main body portion 31 and a grip portion 32 formed of an elastic member, for example, connected to the main body portion 31. A signal cable 21 extends from the proximal end surface side of the grip portion 32. A not shown connector is provided to the proximal end of the signal cable 21 which is detachable with respect to the controller 20 via the connector.

An operation command portion 33 is provided to the side of the main body portion 31. The operation command portion 33 is formed of an operation lever 34 of joy stick type, for example. As the operator tilts the operation lever 34, the command signal corresponding to the direction and amount of the tilting operation is outputted to the controller 20 from the operation command portion 33 via the signal cable 21. For example, if the operation lever 34 is tilted to the distal end side, the power drive unit 60 is driven under the control of the control unit 25 constituting the controller 20 to drive the sheath 42 of the treatment instrument 40 forward. Meanwhile, if the operation lever 34 is tilted to the proximal end side, the sheath 42 of the treatment instrument 40 is driven by the power drive unit 60 to be reversed under the control of the control unit 25.

Figure 2:
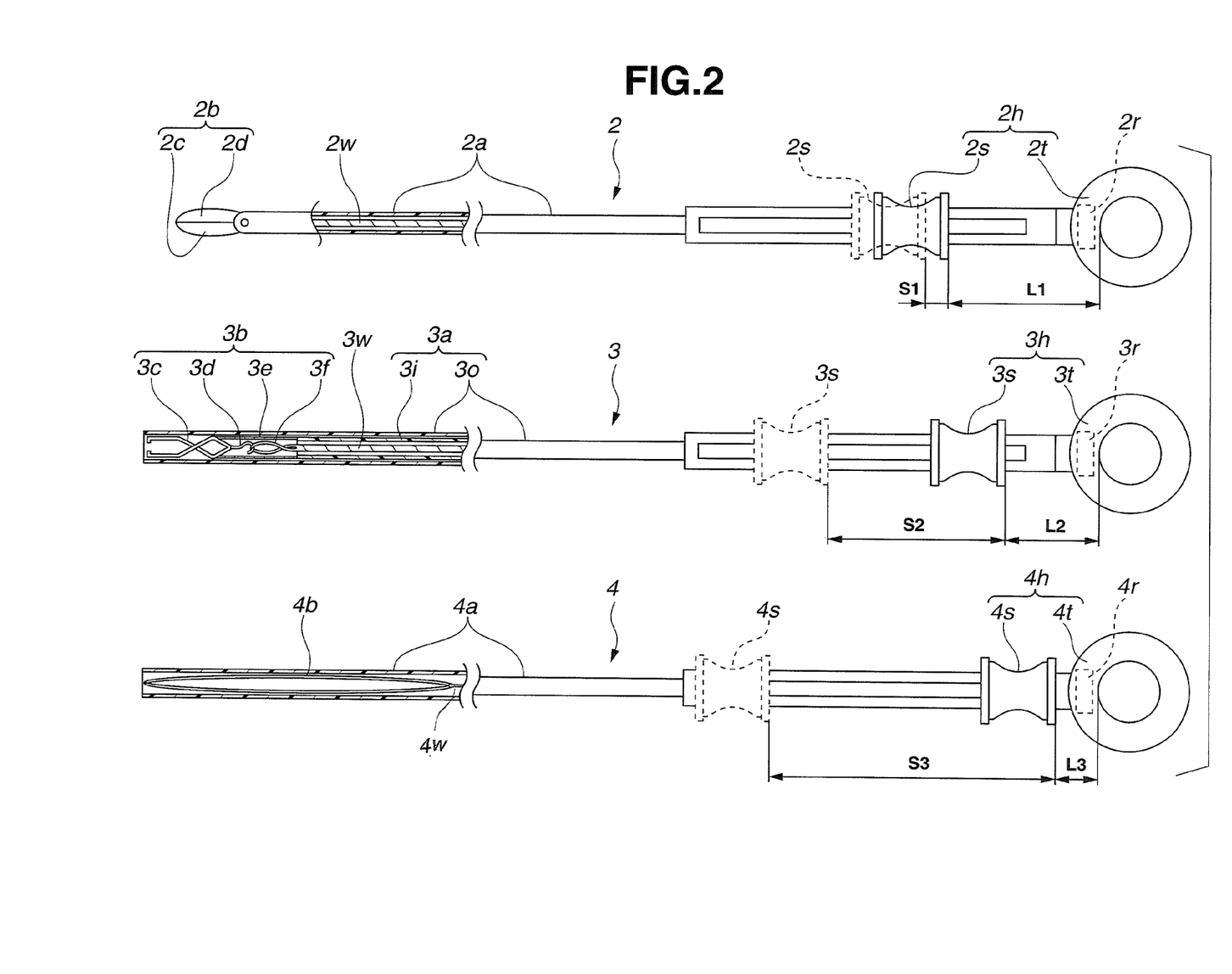
FIG. 2 is an explanatory view showing a structure of a treatment instrument.

As shown in FIG. 2, the treatment instrument 40 may be a biopsy forceps 2, a rotary clip 3, a high frequency snare 4 or the like. In the embodiment, the biopsy forceps is employed as the treatment instrument 40.

The biopsy forceps 2 is equipped with a sheath 2a as a flexible tube which exhibits a predetermined elasticity. The sheath 2a has a thin and long body and a pair of biopsy cups 2c and 2d to form a tissue extraction portion 2b as the treatment section 41 at the distal end. The biopsy cups 2c and 2d are structured to be freely opened and closed by an operation wire 2w inserted in the sheath 2a. The operation wire 2w is structured to be moved back and forth through the operation of a handle 2h as the operation portion.

The handle 2h of the biopsy forceps 2 is formed of a finger ring (hereinafter referred to as a thumb ring) 2t and a slider 2s. The finger ring 2t includes a hole which accommodates the thumb of the user, for example. The slider 2s has a recess portion where the forefinger, middle finger or ring finger of the user is rested.

The open/close state of the biopsy cups 2c and 2d of the biopsy forceps 2 may be switched by moving the operation wire 2w back and forth through the change in the position of the slider 2s that forms the handle 2h. An installation distance L1 as the initial position between the thumb ring 2t and the slider 2s is set to 39 mm, for example. The maximum displacement distance S1 of the slider 2s from the installation position is set to 9.5 mm, for example.

The rotary clip 3 includes a sheath 3a as a flexible tube which exhibits the predetermined elasticity. The sheath 3a according to the embodiment is formed of an outer sheath 3o and an inner sheath 3i. A clip unit 3b is disposed as the treatment section 41 in the distal end of the outer sheath 30 at the distal end side of the inner sheath 3i.

An operation wire 3w is inserted into the sheath 3a, and moved back and forth through the operation of a handle 3h as the operation portion. The clip unit 3b is formed of a clip 3c, a hook 3d and a clip clamp tube (hereinafter referred to as a clamp tube) 3e. The hook 3d is grappled with a loop 3f provided to the distal end of the operation wire 3w within the sheath 3a.

The handle 3h of the rotary clip 3 is formed of a thumb ring 3t having a hole and a slider 3s having a recess portion. In the clip unit 3b of the rotary clip 3, the clip 3c is opened by moving the inner sheath 3i forward with respect to the outer sheath 3o. Then the slider 3s that forms the handle 3h is displaced to pull the operation wire 3w to the hand side of the operator so as to deform the clip 3c to be closed. The hook 3d is then disengaged from the loop 3f. In the rotary clip 3, an installation distance L2 as the initial distance between the thumb ring 3t and the slider 3s is set to 27 mm, and the maximum displacement distance S2 of the slider 3s is set to 52 mm, for example.

A high frequency snare 4 includes a sheath 4a as a flexible tube which exhibits the predetermined elasticity. The thin and long sheath 4a includes a snare section 4b as the treatment section 41 at the distal end. The snare section 4b is retractably provided to the distal end of the sheath 4a. An operation wire 4w which extends from the snare section 4b is inserted in the sheath 4a. The operation wire 4w is moved back and forth through the operation of a handle 4h as the operation portion.

The handle 4h of the high frequency snare 4 is formed of a thumb ring 4t having a hole and a slider 4s having a recess portion. The snare section 4b of the high frequency snare 4 is moved out of the distal end of the sheath 4a to form a loop in response to the forward movement of the slider 4s of the handle 4h. Meanwhile, when the slider 4s is reversed from the aforementioned state, the loop-like snare section 4b is stored in the sheath 4a. In the high frequency snare 4, an installation distance L3 as the initial position of the thumb ring 4t and the slider 4s is set to 3 mm, and the maximum displacement distance S3 of the slider 4s is set to 92 mm, for example. A not shown high frequency wiring cord is electrically coupled with the slider 4s of the high frequency snare 4 employed in the present embodiment.

As described above, each installation distance and the maximum displacement distance of the aforementioned treatment instrument is different depending on the type. The installation distance of the treatment instrument of the same type may be slightly different depending on the model.

In the embodiment, IC chips with built in treatment instrument ID (hereinafter referred to as RFID, that is, Radio Frequency Identification) 2r, 3r and 4r, for example, the integrated circuit are provided in predetermined positions of the thumb ring 2t which forms the handle 2h of the biopsy forceps 2, the thumb ring 3t which forms the handle 3h of the rotary clip 3, and the thumb ring 4t which forms the handle 4h of the high frequency snare 4, respectively serving as the treatment instrument identification sections, each of which stores the treatment instrument information.

The RFID 2r stores registered treatment instrument information, that is, the information with respect to the model of the biopsy forceps 2. The RFID 3r stores registered information with respect to the model of the rotary clip 3. The RFID 4r stores registered information with respect to the model of the high frequency snare 4.

The power drive unit 60 shown in FIG. 1 is provided detachably with respect to the treatment instrument port 19 of the endoscope 10, for example. The power drive unit 60 is electrically coupled with or decoupled from the controller 20 via an electric cable 24 through which the signal wire is inserted.

The power drive unit 60 includes a pair of rollers 62 and 63 in an enclosure 61 as shown by dashed lines. The rollers 62 and 63 are formed of elastic resin members, respectively, one of which is driven by a motor (not shown) as a not shown drive source.

The sheath 42 of the treatment instrument 40 is interposed between the pair of rollers 62 and 63 under pressure. When the motor is driven in the state where the sheath 42 is interposed between the rollers 62 and 63, the sheath 42 interposed between two rollers 62 and 63 is moved back and forth in the treatment instrument channel 14a of the endoscope 10 with the rotation of the roller 62, for example.

The control unit 25 of the controller 20 serves to control the driving operation of the motor of the power drive unit 60 based on the operation of the operation lever 34 of the control 30.

Figure 3:
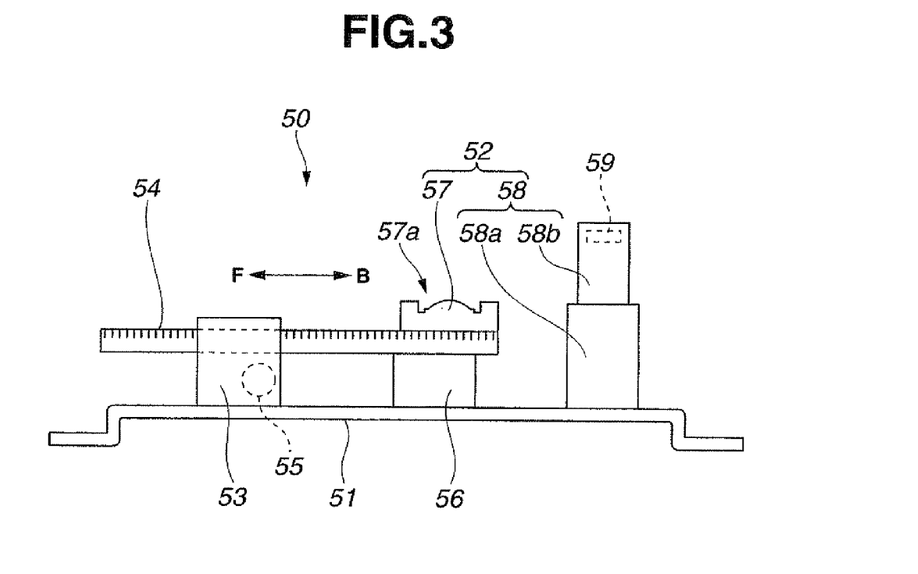
FIG. 3 is a side view showing the structure of the treatment instrument operation unit.
Figure 4:
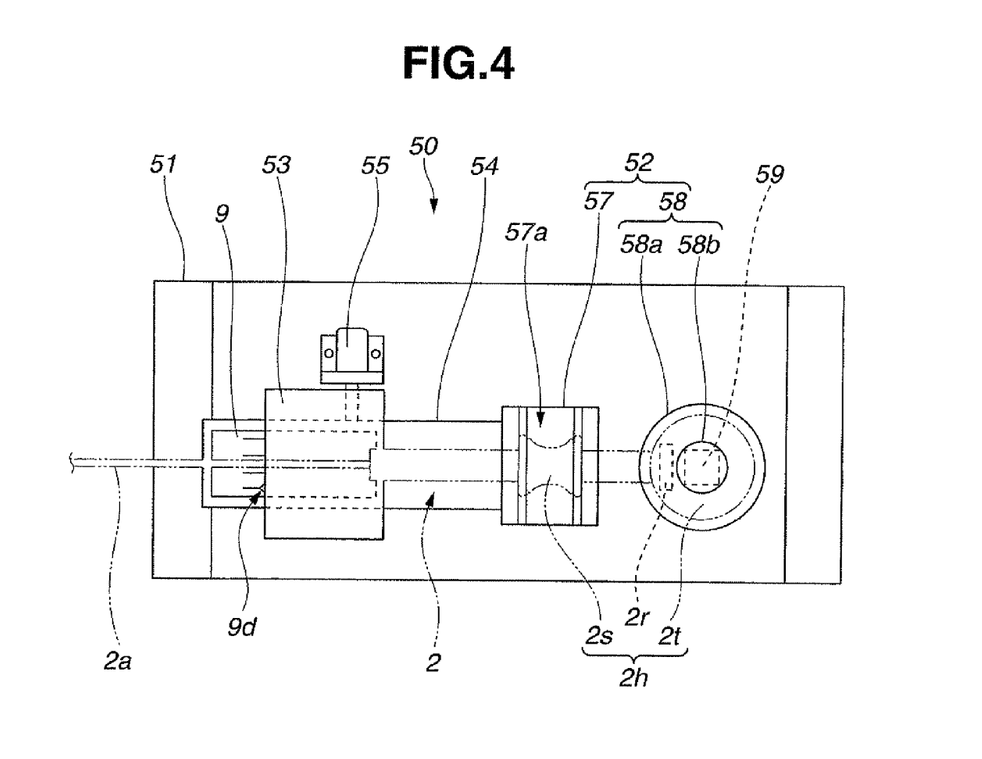
FIG. 4 is a plan view showing the structure of the treatment instrument operation unit.

Referring to FIGS. 1, 3 and 4, the treatment instrument operation unit 50 includes a base body 51 on which an operation portion installation section 52 formed of first and second holding portions, a treatment section operation box 53, and a mount section 56 to be described later are disposed.

The treatment section operation box 53 is fixed to the base body 51. A rack 54 with linear teeth is movably attached to the treatment section operation box 53. The treatment section operation box 53 is provided with a motor 55. A pinion gear in mesh with the linear teeth of the rack 54 is fixed to a motor shaft of the motor 55.

In the state where the pinion gear is meshed with the linear teeth of the rack 54, the motor 55 is rotated such that the driving force thereof is transmitted to the rack 54 via the pinion gear. The rack 54 is then moves back and forth in the longitudinal direction as shown by an arrow direction in FIG. 3. In other words, the rack 54 serves as the drive section.

The treatment section operation box 53 is connected to one end of the electric cable 23. The other end of the electric cable 23 is connected to the controller 20 so as to be electrically coupled thereto or decoupled therefrom.

In the embodiment, the motor 55 in the treatment section operation box 53 is driven by tilting the operation lever 34 provided to the control 30 in the direction orthogonal to the longitudinal direction of the operation lever 34, that is, the lateral direction. For example, the motor 55 of the treatment section operation box 53 is rotated by tilting the operation lever 34 to the right of the front of the control 30 such that the rack 54 is moved in the arrow F direction.

A slider holding portion (hereinafter referred to as a holding portion) 57 as the first holding portion of the operation portion installation section 52 is provided to the proximal end of the rack 54. The holding portion 57 is integrally fixed to the rack 54 with a screw. The holding portion 57 has a holding groove 57a for accommodating the slider 2s which forms the handle 2h of the biopsy forceps 2, the slider 3s of the rotary clip 3, or the slider 4s of the high frequency snare 4.

A ring pressing portion 58 as the second holding portion of the operation portion installation section 52 includes a thumb ring mount (hereinafter referred to as a mount portion) 58a and a thumb ring hole insertion protrusion 58b (hereinafter referred to as a protrusion). The mount portion 58a is integrally fixed to the base body 51 with the screw. The protrusion 58b is inserted into the hole of the thumb ring 2t which forms the handle 2h of the biopsy forceps 2, the hole of the thumb ring 3t of the rotary clip 3, or the hole of the thumb ring 4t of the high frequency snare 4.

The hole of the thumb ring 2t which forms the biopsy forceps 2 is set to face the protrusion 58b so as to be moved downward. The thumb ring 2t is then placed on an upper surface 58u of the mount portion 58a so as to be installed. In the aforementioned installation state, the slider 2s is positioned in the holding groove 57a of the holding portion 57 as shown in FIG. 1, that is, the handle 2h of the biopsy forceps 2 is integrally fixed to the operation portion installation section 52 of the treatment instrument operation unit 50.

An RFID reader 59 serving as a treatment instrument ID reading sensor is provided in the protrusion 58b of the ring pressing portion 58, which serves as the treatment instrument information obtaining unit for reading the treatment instrument information with respect to the RFIDs 2r, 3r and 4r disposed in the thumb rings 2t, 3t and 4t, respectively. One end of a communication cable 22 is connected to the ring pressing portion 58, and the other end is connected to the controller 20 so as to be electrically coupled thereto or decoupled therefrom.

When the thumb ring 2t of the biopsy forceps 2 as the treatment instrument 40 is brought to be close to the protrusion 58b, the RFID reader 59 reads the treatment instrument information with respect to the RFID2r provided in the thumb ring 2t. The RFID reader 59 outputs the thus read treatment instrument information to the controller 20 via the communication cable 22. That is, the RFID reader 59 serves as a command signal output section for outputting the treatment instrument information functioning as the installation start signal which notifies that the installation of the treatment instrument 40 to the treatment instrument operation unit 50 has begun.

The communication cable 22 may be combined with the electric cable 23 connected to the aforementioned treatment section operation box 53 as the composite signal cable.

The controller 20 according to the embodiment is formed of the control unit 25 serving as a CPU, a memory unit 26 serving as a treatment instrument information memory unit such as a hard disk, a signal output section 27, and a not shown signal input section.

The memory unit 26 stores operation programs for the respective models required to operate the treatment instrument in accordance with the model information, each length of the sheaths 2a, 3a and 4a, installation distances L1, L2 and L3 between the thumb rings 2t, 3t and 4t, and the sliders 2s, 3s and 4s upon installation of the handles 2h, 3h and 4h as the position information of the operation portion, respectively and maximum displacement distances S1, S2 and S3 of the sliders 2s, 3s and 4s from the thumb rings 2t, 3t and 4t, respectively dependent on the model information.

The operation program for operating the treatment instrument includes the program for coinciding the distance between the holding portion 57 and the protrusion 58b with the installation distance of the operation portion which is different depending on the model by adjusting the relative distance between the holding portion 57 and the protrusion 58b by driving the motor 55, the program for operating the treatment instrument inserted into the body cavity via the treatment instrument channel 14a of the endoscope 10 of the operation portion likewise the operation performed by the experienced operator, and the like. In the embodiment, the memory unit 26 stores the operation programs, for example, the biopsy forceps program, the rotary clip program, the high frequency snare program, and the like.

The control unit 25 is formed of a memory unit, an operation processing section and a determination section. The signal input section is formed of a treatment instrument information acquiring section, an operation lever signal determination section, a motor rotating speed acquiring section, and the like.

The signal output section 27 is formed of an output section for the treatment instrument operation unit, and an output section for the power drive unit. The output section for the treatment instrument operation unit outputs the control signal for setting the installation distance to the treatment instrument operation unit 50, or the control signal for operating the treatment section 41 based on the tilt signal of the operation lever 34. The output section for the power drive unit outputs the control signal for driving to rotate the roller 62 of the power drive unit 60 based on the tilt signal of the operation lever 34.

A lamp (not shown) for supplying the illumination light and a signal processing circuit (not shown) and the like are provided in the controller 20. The signal processing circuit executes the process for generating the drive signal which drives the image pickup device such as the CCD provided to the distal end of the endoscope, and the process for generating the electric signal transferred from the image pickup device into the video signal. The controller 20 is connected to a display unit such as a liquid crystal display (not shown) for displaying the endoscopic image.

Figure 5:
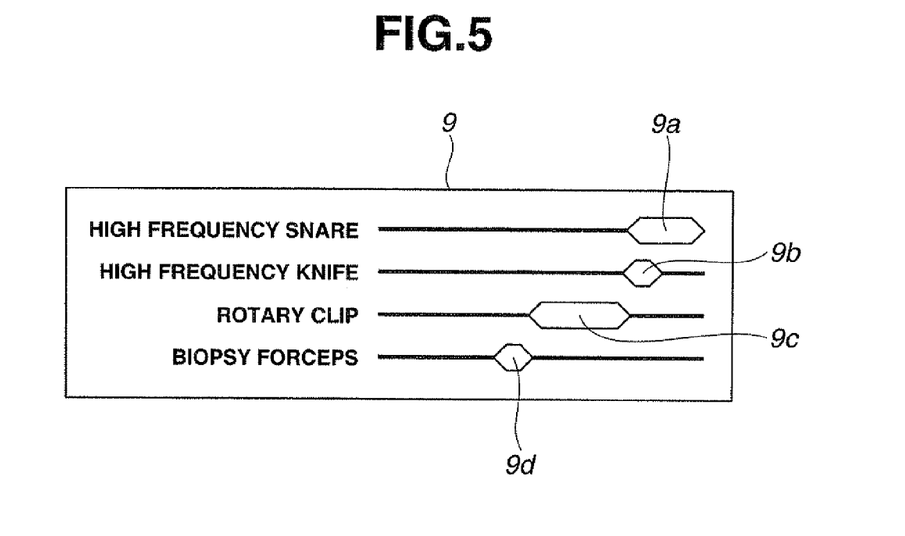
FIG. 5 is an explanatory view showing a label for visual identification of a slider holding portion.

A reference numeral 9 shown in FIG. 4 denotes a label indicating the slider holding portion (hereinafter referred to as a visual identification label). The visual identification label 9 is placed on the surface of the distal end side of the movable rack 54. Referring to FIG. 5, indexes 9a, 9b, 9c and 9d each indicating the range for arranging the holding portion 57 suitable for the respective types of the treatment instrument are provided on the surface of the visual identification label 9.

As the visual identification label 9 is put on the surface of the rack 54, for example, the distal end of the treatment section operation box 53 is positioned within the index 9d as shown in FIG. 4, the operator is allowed to visually identify that the holding portion 57 provided at the proximal end of the rack 54 has been moved to the position suitable for installing the biopsy forceps.

The action of the medical system 1 equipped with the above-structured treatment instrument operation unit 50 will be described hereinafter.

The staff connects the signal cable 21, the communication cable 22, and the electric cables 23, 24 to the controller 20 for the use of the medical system 1 in the operation. After connecting the cables, the controller 20 is turned ON.

Then the staff installs the treatment instrument used in the operation such as the biopsy forceps 2 in the treatment instrument operation unit 50. The staff brings the thumb ring 2t which forms the handle 2h of the biopsy forceps 2 to be close to the protrusion 58b of the ring pressing portion 58 as shown in the transition from the dashed line to the solid line in FIG. 6 such that the hole of the thumb ring 2t is placed to face the protrusion 58b. Thereafter, the thumb ring 2t is moved toward the upper surface 58u of the mount portion 58a.

Figure 6:
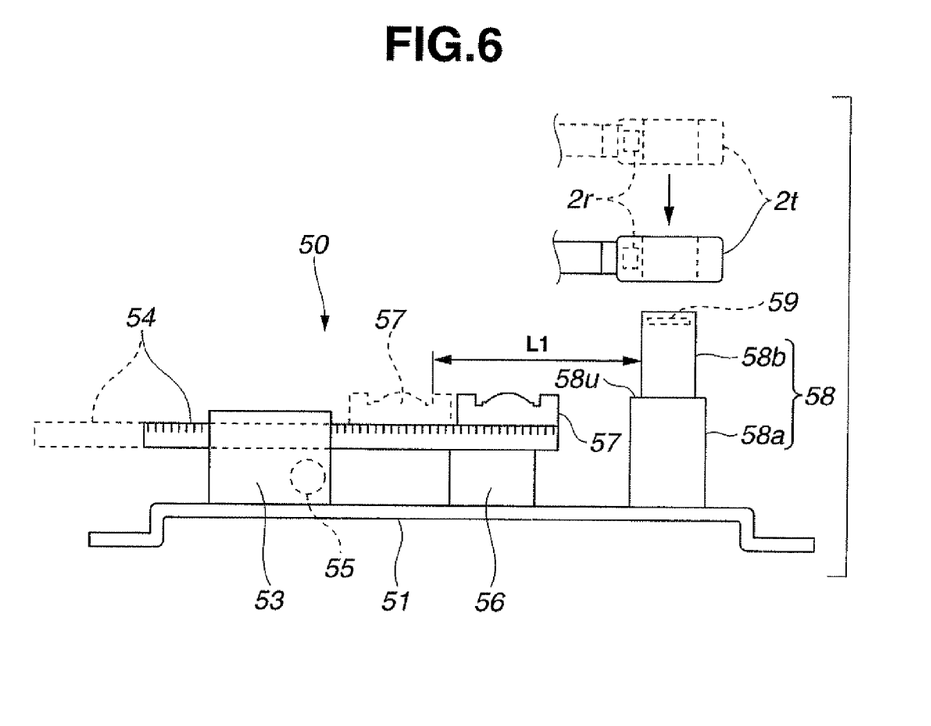
FIG. 6 is an explanatory view showing the operation of the treatment instrument operation unit.

As the thumb ring 2t is brought to be close to the protrusion 58b, the RFID reader 59 installed in the protrusion 58b obtains the treatment instrument information of the RFTD2r of the thumb ring 2t, that is, the model information. The RFID reader 59 immediately outputs the obtained treatment instrument information to the treatment instrument information acquiring section of the controller 20.

When the treatment instrument information is input to the treatment instrument information acquiring section, the control unit 25 determines that the installation of the treatment instrument to the treatment instrument drive unit has begun, and obtains the biopsy forceps program for operating the treatment instrument corresponding to the model information, the length of the sheath, the installation distance L1 between the thumb ring and the slider upon the installation, the maximum displacement distance S1 and the like from various registered data in the memory unit 26.

Thereafter, the control unit 25 outputs the control signal from the signal output section 27 to the treatment instrument operation unit 50. Then the motor 55 in the treatment section operation box 53 is rotated such that the holding portion 57 integrally fixed to the rack 54 is displaced by a predetermined distance in the predetermined direction for positional adjustment. More specifically, the holding portion 57 which forms the operation portion installation section 52 as shown by the solid line is displaced to the position shown by the dashed line such that the distance between the holding portion 57 and the protrusion 58b of the ring pressing portion 58 is set to the installation distance L1 between the thumb ring 2t and the slider 2s which forms the handle 2h of the biopsy forceps 2.

The distance between the holding portion 57 and the protrusion 58b is set to the installation distance L1 after the output of the treatment instrument information to the control unit 25 from the RFID reader 59 during the movement of the thumb ring 2t toward the upper surface 58u of the mount portion 58a.

The distance between the holding portion 57 and the protrusion 58b obtained when the thumb ring 2t is placed on the upper surface 58u of the mount portion 58a is set to the installation distance L1. The slider 2s is set in the holding groove 57a of the holding portion 57 simultaneously with the moment when the thumb ring 2t is placed on the upper surface 58u of the mount portion 58a. Thereby, the installation of the biopsy forceps 2 to the treatment instrument operation unit 50 is completed. The staff then inserts the sheath 2a of the biopsy forceps 2 into the treatment instrument channel 14a of the endoscope 10 via the power drive unit 60.

Thereafter, the operator tilts the operation lever 34 of the control 30 while observing the endoscopic image such that the insertion portion 14 of the endoscope 10 having the biopsy forceps 2 inserted into the treatment instrument channel 14a is inserted into the target site in the body cavity of the subject. The operator brings the distal end portion of the insertion portion 14 to face the tissue of the target site, and collects the tissue by tilting the operation lever 34 while observing the endoscopic image.

The maximum displacement distance S1 is obtained so as to prevent the slider 2s from displacing by the amount in excess of such value.

Thus, the RFID which stores the model information as the treatment instrument information is installed in the thumb ring which forms the operation portion of the treatment instrument, and the RFID reader for reading the model information stored in the RFID is installed on the protrusion which forms the operation portion installation section of the treatment instrument operation unit. Thus, in the case where the treatment instrument is installed in the treatment instrument operation unit, as the thumb ring is brought to be close to the protrusion, the RFID reader obtains the model information of the RFID. The obtained model information is immediately outputted to the controller. This allows the controller to obtain the model information of the treatment instrument before arranging a part of the treatment instrument in the treatment instrument operation unit.

The memory unit disposed in the controller is designed to preliminarily store not only the operation program for operating the treatment instrument but also such information as the distance between the thumb ring and the slider upon installation of the treatment instrument, and the maximum displacement distance for the respective models. Then, after the model information is inputted to the controller, the controller obtains the program corresponding to the model information and various information data under the control of the control unit so as to output the control signal corresponding to the treatment instrument information from the signal output section to the treatment instrument operation unit. This makes it possible to set the distance between the holding portion and the protrusion which forms the operation portion installation section of the treatment instrument operation unit to the distance stored in the memory unit before placing the thumb ring of the treatment instrument on the upper surface of the mount portion.

Thus, the adjustment operation for coinciding the installation position of the operation portion installation section of the treatment instrument operation unit with the operation portion of the treatment instrument which has been performed by the staff upon setting of the treatment instrument to the treatment instrument operation unit may be eliminated. In other words, the work for installing the treatment instrument in the treatment instrument operation unit may be simplified.

In the aforementioned embodiment, the RFID reader is provided in the protrusion of the ring pressing portion which forms the treatment instrument operation unit 50, and the RFID is installed in the thumb ring of the handle which forms the treatment instrument. However, a treatment instrument operation unit 50A equipped with a treatment instrument identification unit (hereinafter referred to as a selector) 70 may be structured as shown in FIG. 7.

Figure 7:
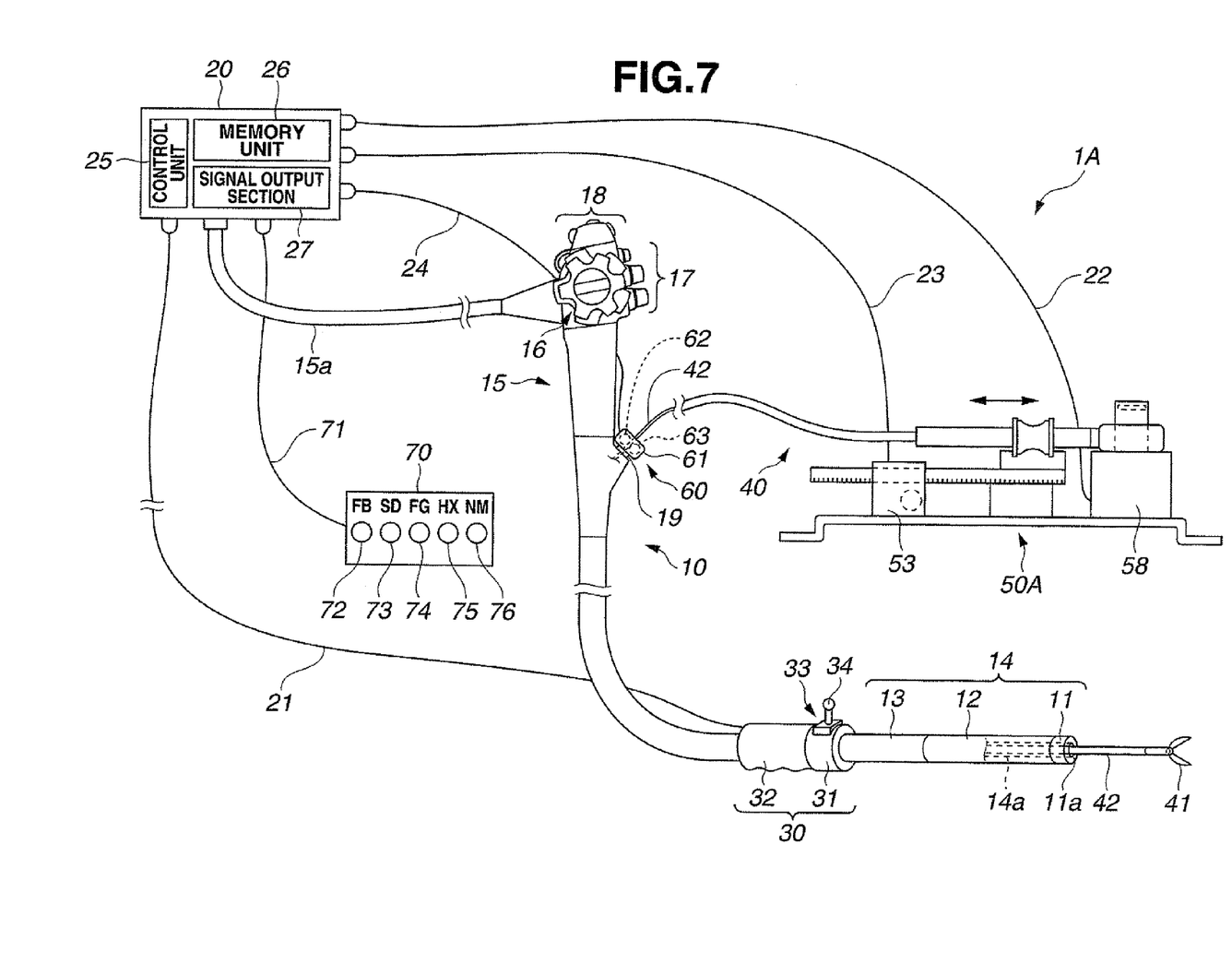
FIG. 7 is an explanatory view showing the medical system equipped with the treatment instrument operation unit including the treatment instrument identification unit.

The treatment instrument operation unit 50A shown in FIG. 7 is equipped with a selector 70. The selector 70 is electrically coupled with or decoupled from the controller 20 via a signal cable 71. The selector 70 includes plural treatment instrument selector portions (hereinafter referred to as buttons) 72, 73, 74, 75 and 76. When the staff depresses the button corresponding to the treatment instrument to be installed to the treatment instrument operation unit 50A, for example, the button 72, the treatment instrument identification information identifying that the treatment instrument is the biopsy forceps is outputted to the signal input section of the controller 20.

Characters, illustrations and codes each indicating the type of the treatment instrument are printed on the portion around the buttons 72, 73, 74, 75 and 76, the upper portion thereof, for example. In the embodiment, the codes are printed. The printed codes "FB", "SD", "FG", "HX", and "NM" represent the biopsy forceps, the high frequency snare, the grasping forceps, the rotary clip device, and the injection needle, respectively. The selector 70 is provided with a button for balloon catheter coded as "B", the button for the high frequency knife coded as "KD" and the like in addition to the aforementioned buttons.

Other structure is the same as that of the aforementioned embodiment. The same members as those in the embodiment are designated with the same codes, and explanations thereof, thus, will be omitted.

The action of a medical system 1A equipped with the treatment instrument operation unit 50A having the above-structured selector 70 will be described.

Upon the use of the medical system 1A for the operation, the staff connects the signal cables 21, 71, the communication cable 22, and the electric cables 23, 24 to the controller 20. The controller 20 is then turned ON.

Then the staff depresses the button 72 on the selector 70 for installing the treatment instrument used for the operation to the treatment instrument operation unit 50A, that is, the biopsy forceps 2, for example. Then, the selector 70 outputs the treatment instrument information to the treatment instrument information acquiring section of the controller 20.

When the treatment instrument information is inputted to the treatment instrument information acquiring section, the control unit 25 immediately obtains the biopsy forceps program for operating the treatment instrument, the length of the sheath 2a, the installation distance L1 between the thumb ring and the slider upon the installation, and the maximum displacement distance S1 from various data stored in the memory unit 26.

Thereafter, the control unit 25 outputs the control signal from the signal output section 27 to the treatment instrument operation unit 50A. Then, the motor 55 in the treatment section operation box 53 is then rotated to displace the holding portion 57 integrally fixed to the rack 54 by a predetermined distance in the predetermined direction. The distance between the holding portion 57 which forms the operation portion installation section 52 and the protrusion 58b of the ring pressing portion 58 is set to the installation distance L1 between the thumb ring 2t and the slider 2s which form the handle 2h of the biopsy forceps 2. This makes it possible to easily install the biopsy forceps 2 in the treatment instrument operation unit 50A.

The biopsy forceps 2 may be installed in the treatment instrument operation unit 50A after the staff confirms whether or not the rack 54 has been displaced to the biopsy forceps installation position by visually identifying the visual identification label 9.

The use of the selector connected to the controller makes it possible to easily install the treatment instrument equipped with no RFID in the treatment instrument operation unit.

Other functions and effects are the same as those described in the aforementioned embodiment.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical system comprising:
   plural types of treatment instruments provided with different treatment sections and having different installation distances of operation portions for operating the treatment sections;
   a treatment instrument operation unit provided with a drive unit for driving the operation portion of the treatment instruments, an operation portion installation section provided to the drive unit, to which the operation portion is attached, and a command signal output section for outputting an installation start signal indicating a start of the treatment instrument installation upon installation of the operation portion in the operation portion installation section; and
   a controller to which the treatment instrument operation unit is connected, which includes:
      a treatment instrument information memory unit for storing data of the treatment instrument information including an installation distance indicating a position of the operation portion preliminarily set depending on the type and the model of the treatment instrument, and a maximum displacement distance; and
      a signal output section for obtaining the treatment instrument information corresponding to the installation start signal from data of information with respect to the treatment instruments stored in the treatment instrument information memory unit to output a control signal to the drive unit based on the installation start signal outputted from the command signal output section;
   wherein the operation portion is an operation handle having a thumb ring and a slider, the operation portion installation section includes a first holding portion for holding the slider which forms the operation handle, and a second holding portion for holding the thumb ring which forms the operation handle; and
   the drive unit moves one of the first and the second holding portions based on the control signal outputted from the controller to the drive unit to set a distance between the thumb ring and the slider which form the operation handle to the installation distance.

2. The medical system according to claim 1, further comprising:
   a treatment instrument identification section provided in the corresponding operation portion of the treatment instrument, which stores the treatment instrument information for identifying a type and a model of the treatment instrument; and
   a treatment instrument information acquiring section which acquires the treatment instrument information stored in the treatment instrument identification section in a noncontact manner to serve as the command signal output section for outputting the installation start signal which contains the treatment instrument information to the controller.

3. The medical system according to claim 1, wherein the thumb ring includes the treatment instrument identification section, and the second holding portion includes the treatment instrument information acquiring section.

4. The medical system according to claim 1, wherein displacement amount of the thumb ring and the slider displaced by the drive unit during an operation is limited depending on each treatment instrument based on the information of the maximum displacement distance contained in the treatment instrument information obtained by the treatment instrument information acquiring section.

5. A medical system comprising:
   plural kinds of treatment instruments provided with different treatment sections and having different installation distances of operation portions for operating the treatment sections;
   a treatment instrument operation unit including a drive unit for driving the operation portion which operates the treatment sections provided to the treatment instruments, and an operation portion installation section for installing the operation portion to the drive unit;
   a treatment instrument identification unit provided with plural treatment instrument selectors for outputting data of treatment instrument identification information for identifying a type of the treatment instrument to be installed in the operation portion installation section upon installation of the operation portion in the operation portion installation section of the treatment instrument operation unit; and
   a controller provided with a treatment information memory unit for storing data of the treatment instrument information including an installation distance indicating a position of the operation portion preliminarily set depending on the type of the treatment instrument, and a maximum displacement distance, and a signal output section for obtaining the treatment instrument information with respect to the treatment instrument corresponding to the treatment instrument identification information inputted to the controller from data of information with respect to the treatment instruments stored in the treatment instrument information memory unit to output a control signal for setting the operation portion installation section to the installation distance to the drive unit,
   wherein the operation portion is an operation handle having a thumb ring and a slider, the operation portion installation section includes a first holding portion for holding the slider which forms the operation handle, and a second holding portion for holding the thumb ring which forms the operation handle; and
   the drive unit moves one of the first and the second holding portions based on the control signal outputted from the controller to the drive unit to set a distance between the thumb ring and the slider which form the operation handle to the installation distance.

* * * * *